US00PP12159P2

(12) United States Plant Patent
Heims

(10) Patent No.: US PP12,159 P2
(45) Date of Patent: Oct. 23, 2001

(54) ***X HEUCHERELLA* PLANT NAMED 'BURNISHED BRONZE'**

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/452,024

(22) Filed: Nov. 30, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman Campbell Leigh & Whinston LLP

(57) ABSTRACT

A new and distinct hybrid of *x Heucherella* plant characterized by a unique combination of glossy, dark bronze-brown coloration on large cut foliage.

1 Drawing Sheet

The present invention relates to a new and distinct intergeneric hybrid of Heuchera and Tiarella, of the family Saxifragaceae, which originated as a cross between an unpatented Heuchera named 'Black Beauty' (seed parent) and an unpatented, unnamed Tiarella hybrid seedling (pollen parent). Due to the fact that the instant plant and parent plants are the result of crosses between several different Heuchera and/or Tiarella species, no species designations are given.

This new *x Heucherella* plant is a result of a controlled cross of the aforementioned plants in Canby, Oreg. This hybrid was chosen from a large selection of seedlings. Seed and pollen parent plants were retained to observe habit and to compare with the instant plant. The new variety has been reproduced only by asexual propagation (division and tissue culture). Each of the progeny exhibits identical characteristics to the original plant.

This plant is characterized by the following:

1. Glossy bronze-brown foliage.
2. Large cut leaves.

Asexual propagation by division and tissue culture, as done in Canby, Oreg., shows that the foregoing characteristics and distinctions come true to form and are established and transmitted through succeeding propagations.

The drawing shows *x Heucherella* 'Burnished Bronze' in May in Canby, Oreg.

The following is a detailed description of the new *x Heucherella* hybrid based on observations of 1.5 year-old specimens growing in the field in Canby, Oreg. The color descriptions are all based on The Royal Horticultural Society Colour Chart.

Foliage:

*Type.*—Simple. Semi-evergreen (evergreen in USDA zones 6 and above, deciduous in USDA zones 4 and 5).
*Shape.*—Cordate. Palmately lobed. Individual lobes are cleft. The central lobe may twist.
*Length.*—8–9 cm.
*Width.*—7–9 cm.
*Petiole length.*—14.5 cm.
*Margins.*—Dentate-serrate-undulate. Ciliolate.
*Apex.*—Acute.
*Base.*—Cordate.
*Leaf texture.*—Puberulent.
*Petiole texture.*—Pubescent.

*Leaf arrangement.*—Rosette.
*Venation.*—Reticulate.

Flower:

*Type.*—Imperfect. Incomplete. Anthers not present.
*Shape.*—Stellate.
*Overall size.*—8 mm wide and 5 mm deep.
*Petal count.*—5.
*Petal shape.*—Lanceolate to elliptic with a clawed base. Petals sometimes incised.
*Petal size.*—About 1.5 mm wide and 3 mm long.
*Sepal shape.*—Petaloid. Oblong where parted. Fused at or near receptacle.
*Sepal number.*—5 lobes.
*Sepal size.*—Slightly over 1 mm wide where parted and to 5 mm long from sepal tip to pedicel.
*Ovary position.*—Partly inferior.
*Carpel number.*—2.
*Inflorescence type.*—Thryse.
*Flower number per inflorescence.*—50–100.
*Peduncle width.*—3 mm tapering to 1 mm.
*Peduncle texture.*—Glandular pubescent.
*Blooming height.*—47 cm.
*Bloom period.*—May to July.
*Fragrance.*—None.

Size:

*Height.*—23 cm (2 year old plant grown in Canby, Oreg.).
*Width.*—43 cm (2 year old plant grown in Canby, Oreg.).

Fruit: No fruit or seed produced.
*Fertility.*—Sterile.

Habit: Clumping.

Disease: Diseases Have not been observed on plants grown in Canby, Oreg.

Hardiness: Cold hardy to USDA Zone 4.

Color characteristics:

*Foliage.*—Upper surface — RHS 200A Brown Group. The lower half of some leaves display RHS 137A Green Group. Upper surface, along veins — RHS200A Brown Group. Lower surface — RHS 187A Greyed-Purple Group.
*Flower.*—Bud — RHS 39C to 36A Red Group. Petal — Close to RHS 62D Red-Purple Group but lighter. Sepal — RHS 66C Red-Purple Group at tip and receptacle but RHS 62D Red-Purple Group in-between. Ovary — RHS 65C–D Red-Purple Group.

*Peduncle.*—RHS 187C Greyed-Purple Group at the apex fading to RHS 148A Yellos-Green Group at the base.

DESCRIPTION OF PARENT PLANTS

The instant plant resulted from a cross between Heuchera 'Black Beauty' and a Tiarella hybrid seedling. Heuchera 'Black Beauty' was selected as a parent plant for its shiny deep burgundy-red foliage. The instant plant differs from Heuchera 'Black Beauty' in having leaves that are much more cut and is smaller in size. The Tiarella hybrid seedling was selected for its leaves with a dark center blotch. The instant plant differs from the Tiarella hybrid seedling in having leaves that are completely dark colored but display less lobing than its parent.

I claim:

1. A new and distinct hybrid of *x Heucherella* plant substantially as shown and described, characterized by a unique combination of glossy, dark bronze-brown coloration on large cut foliage.

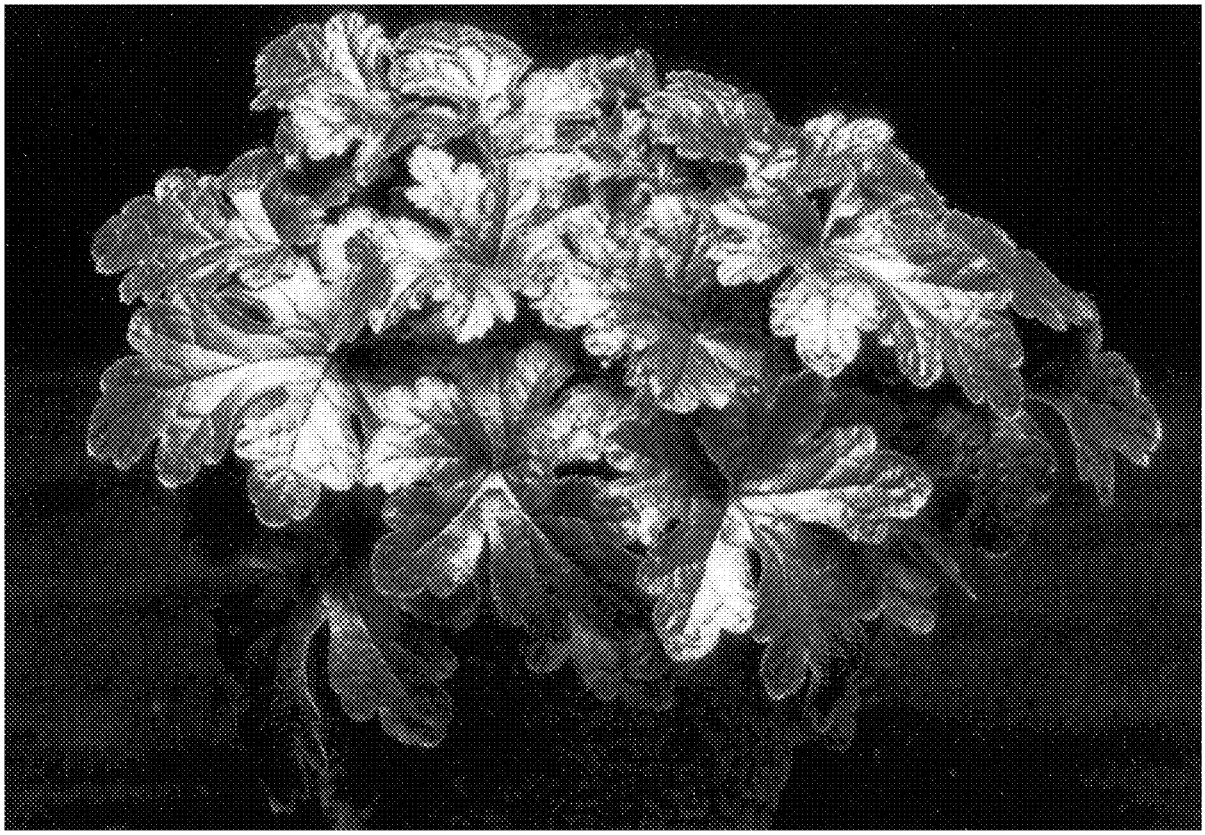

* * * * *